United States Patent
Sato et al.

[11] 3,954,729
[45] May 4, 1976

[54] PROCESS FOR PREPARING A THIOLCARBAMATE

[75] Inventors: Zenichi Sato, Shimizu; Keiichiro Takagi; Masamichi Shimizu, both of Shizuoka, all of Japan

[73] Assignee: Ihara Chemical Industry Co., Ltd., Tokyo, Japan

[22] Filed: Mar. 25, 1974

[21] Appl. No.: 454,619

[52] U.S. Cl. ................ 260/239 B; 260/501.15; 260/326.83; 260/293.51; 260/247.1 T; 260/455 A
[51] Int. Cl.$^2$ .................................. C07C 155/02
[58] Field of Search...... 260/455 A, 501.15, 326.83, 260/293.51, 247.1 T

[56] References Cited
UNITED STATES PATENTS

| | | | |
|---|---|---|---|
| 3,151,119 | 9/1964 | Grisley et al. | 260/455 A |
| 3,167,571 | 1/1965 | D'Amico et al. | 260/455 A |

OTHER PUBLICATIONS
Chem. Abstract, Vol. 37, p. 6826$^8$.

*Primary Examiner*—Elbert L. Roberts
*Assistant Examiner*—D. R. Phillips
*Attorney, Agent, or Firm*—Oblon, Fisher, Spivak, McClelland & Maier

[57] ABSTRACT

Thiolcarbamates are prepared by reacting a secondary amine having the formula

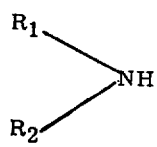

wherein $R_1$ and $R_2$ are the same or different and each represent hydrogen, lower alkyl, alkoxy, alkenyl, alkoxyalkyl, cycloalkyl, hydroxyalkyl, benzyl or phenyl or $R_1$ and $R_2$ combined is a nitrogen containing heterocyclic ring with carbonylsulfide to form an intermediate of an amine salt of a thiolcarbamic acid having the formula

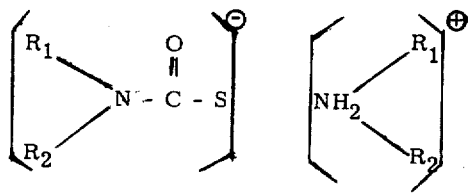

wherein $R_1$ and $R_2$ are defined as above, in an organic solvent having the formula

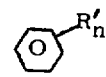

wherein $n$ is 0, 1 or 2 and $R'$ is hydrogen, halogen or a lower alkyl group which solvent is sparingly soluble or insoluble in water and which dissolves the amine salt of the thiolcarbonic acid, and then reacting the intermediate with an alkyl halide having the formula

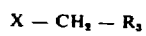

wherein X represents halogen, and $R_3$ represents hydrogen, lower alkyl or naphthyl or phenyl which can be substituted with halogen, alkyl, alkoxy, alkylthio, cyano or nitro, to yield a thiolcarbamate having the formula

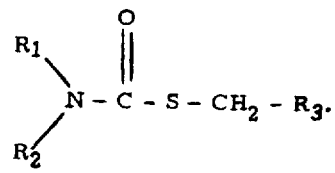

8 Claims, No Drawings

PROCESS FOR PREPARING A THIOLCARBAMATE

BACKGROUND OF THE INVENTION

1. Field of the Invention

This invention relates to the use of thiolcarbamates as herbicides and miticides. More particularly, this invention relates to a process for preparing a high purity thiolcarbamate in high yield by reacting an amine, a carbonylsulfide and an alkyl halide which process avoids pollution problems in industrial drainage.

2. Description of the Prior Art

It is known to prepare thiolcarbamates by a variety of processes including:

1. A secondary amine, carbon monoxide and sulfur are charged into a reactor vessel, and reacted at high temperature and pressure to give an amine salt of the corresponding thiolcarbamic acid. The amine salt of the thiolcarbamic acid thus obtained is then reacted with an alkyl halide to give the thiolcarbamate as shown in the following reaction scheme (U.S. Pat. No. 3,151,119)

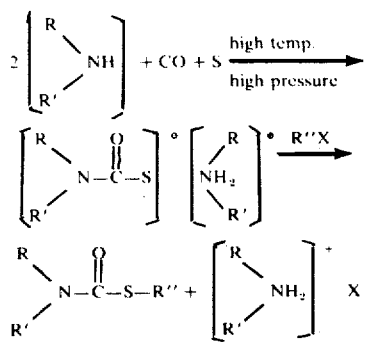

However, because of the low stability of the thiolcarbamic acid amine salt formed in the process as an intermediate, as well as the fact that this process necessarily involves the use of heat and pressure, significant amounts of decomposition products and/or by-products are formed which results in low yields of low purity thiolcarbamate product. Moreover, the most serious drawback with this process is that, as mentioned above, it generates appreciable amounts of undesired products which cause serious ecological problems. Because of the pollution problems posed by this process, it is impractical industrially.

2. In another process, carbonylsulfide is reacted with a secondary amine in the presence of an alkali hydroxide to give an alkali metal salt of thiolcarbamic acid which is further reacted with an alkyl halide in acetone, methanol or ethanol to give a thiolcarbamate as shown by the following reaction scheme (Japanese Patent Publication No. 28427/1973).

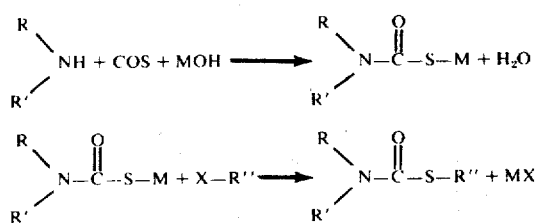

However, the alkali metal salt of thiolcarbamic acid produced in the first step of this process is obtained as an aqueous solution, while the alkyl halide is not soluble in the water system. Accordingly, in order to perform the reaction in a homogeneous system, it is necessary to use a hydrophilic organic solvent such as acetone, methanol or ethanol, which is very undesireable because the hydrophilic organic solvent used unavoidably contaminates the industrial drainage and thereby pollutes rivers. Thus, this process again is not applicable as a practical industrial process because of the ecological problems.

A need, therefore, continues to exist for a method of producing thiolcarbamates which is industrial practical and which overcomes the heretofore longstanding pollution problems.

SUMMARY OF THE INVENTION

Accordingly, one object of the present invention is to provide an improved process for preparing a highly pure thiolcarbamate in yield without serious pollution or contamination problems.

Briefly, this object and other objects of the invention as hereinafter will become more readily apparent can be attained by a process for preparing a thiolcarbamate by reacting a secondary amine having the formula

wherein $R_1$ and $R_2$ are the same or different and each represent hydrogen lower alkyl, alkoxy, alkenyl, alkoxyalkyl, cycloalkyl, hydroxyalkyl, benzyl or phenyl or $R_1$ and $R_2$ combined is a nitrogen containing heterocyclic ring with carbonylsulfide to form an intermediate amine salt of thiolcarbamic acid having the formula

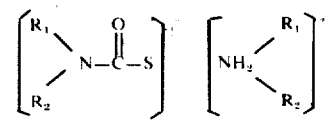

wherein $R_1$ and $R_2$ are defined as above, and then reacting the intermediate with an alkyl halide having the formula

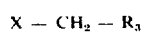

$$X - CH_2 - R_3$$

wherein X represents halogen and $R_3$ represents hydrogen, lower alkyl, or a naphthyl or phenyl which can be substituted with halogen, alkyl, alkoxy, alkylthio, cyano, or nitro to yield a thiolcarbamate having the formula

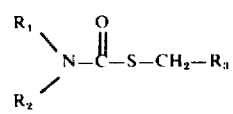

wherein $R_1$, $R_2$ and $R_3$ are defined as above, which process is characterised in that an organic solvent which is sparingly soluble or insoluble in water and which dissolves the amine salt of thiolcarbamic acid is used as the reaction medium.

DETAILED DESCRIPTION OF THE PREFERRED EMBODIMENTS:

The process of the present invention is shown by the following flow diagram.

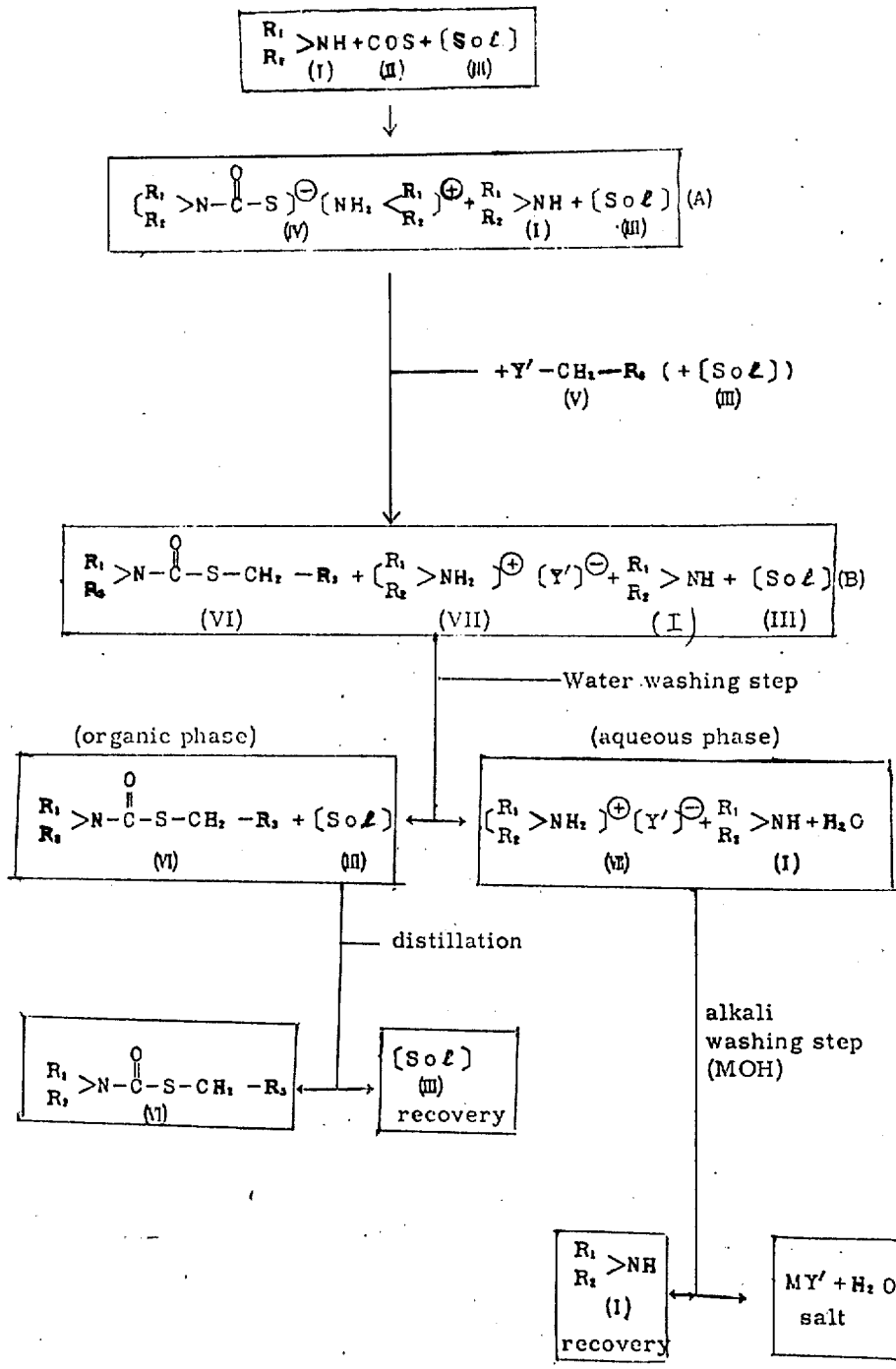

In the reaction sequence, $R_1$, $R_2$, $R_3$ and X are each as defined above, [Sol] represents a special solvent, and MOH represents an alkali hydroxide.

In the process, less than 0.48 mole of carbonylsulfide is reacted with 1.0 mole of the amine (I) in the special solvent (III), whereby a reaction mixture (A) comprising the amine salt of thiol carbamic acid (IV), the unreacted amine (I) and the special solvent (III) is obtained. The amine salt of thiolcarbamic acid (IV) in the mixture (A) is admixed and reacted with a stoichiometrically equivalent amount of the alkyl halide (V) which results in a reaction mixture (B) which comprises the thiolcarbamate (VI), the ammonium salt (VII), the unreacted amine (I), and the special solvent (III). The unreacted amine (I) and the ammonium salt (VIII) are washed from the reaction mixture (B) with water. The aqueous solution containing the unreacted amine (I) and the ammonium salt (VIII) is then washed with an aqueous alkali solution. The amine is separated from the solution by distillation. The mother liquor or the organic solvent phase is distilled to separate high purity, technical thiolcarbamate (VI) from the special solvent (III). Thus, the characteristic features of present invention are: (I) the use of a special organic solvent and (II) the reaction of 0.48 – 0.01, preferably 0.48 – 0.1, especially 0.48 – 0.30 mole of carbonylsulfide per mole of the amine (I). If the carbonylsulfide is used in amounts in excess of 0.48 mole per mole of the amine (I), the amine salt of thiolcarbamic acid (IV) formed is susceptible to decomposition which produces $H_2S$, sulphur, and the like. The decomposition products thus formed react with the alkylhalide (V) to form the monosulfide, $R_3CH_2$—S —$CH_2R_3$ and disulfide, $R_3CH_2$—$S_2$—$CH_2$—$R_3$ as unwanted by-products which decrease the purity of the thiolcarbamate (VI) formed, as well as the yield. If even greater excess amounts of carbonylsulfide are used, such as 0.1 mole of COS per mole of amine, the formation of the amine salt of thiolcarbamic acid (IV) is hindered thus decreasing the yield of the thiolcarbamate (IV) product. In order to minimize the amount of the unreacted amine (I) which is involved in the recovery process while maintaining a high yield of product, it is recommended that the volume of carbonylsulfide to be reacted be within the range of 0.48 –0.30 mole per mole of amine.

The amount of the special organic solvent (III) used in the reaction is preferably 50 g – 500 g per mole of the amine (I). If the amount of the special solvent used is too little, the amine salt of the thiolcarbamic acid formed may precipitate which frustrates the following step. If the amount of the special solvent used is too much, the time for recovering the solvent is lengthened and more energy is required to recover the solvent. When the amine (I) is reacted with the carbonylsulfide, the amine (I) is dissolved in the special solvent (III) and carbonylsulfide (II) is gradually introduced into the constantly agitated amine. The reaction is constantly checked so that the formation of the amine thiolcarbamate salt (IV) is maintained at a level which is less than 96% of the stoichiometric amount of amine initially added. In other words, the reaction is controlled by maintaining the amount of carbonylsulfide added to less than 0.48 mole per mole of amine (I). To check the extent of reaction as mentioned above, the amount of the amine salt (IV) formed is determined by a titration technique using a ½ N-HCl solution and a PH meter on a specific amount of the reaction mixture as a sample. The amount of the amine salt of thiolcarbamic acid formed is calculated by the following equation.

amine salt of thiolcarbamic acid (%) = $\frac{(T_2 - T_1) \times \frac{1}{2} \times f \times M \times \frac{1}{2}}{3 \times S} \times 10^2$, wherein $T_1$ and $T_2$ represent the amounts of ½ N-HCl solution in milliliters required to reach the inflection points on the PH titration curve which correspond to amine salt (IV) and EDA respectively, f represents a factor of ½ N-HCl, M represents the molecular weight of the amine salt of thiolcarbamic acid and S represents the amount of sample from the reaction mixture.

The reaction is performed at 0° – 60°C, preferably 10° – 50°C. If the reaction temperature is greater than the indicated maximum, the amine salt of thiolcarbamic acid (IV) which is formed tends to react with the free amine (I) which remains unreacted to form undesired by-products such as urea derivatives, $H_2S$ and the like.

The second step of the reaction in which the amine salt of thiolcarbamic acid (IV) is reacted with the alkyl halide (V), is performed by adding the alkyl halide dropwise to the agitated reaction mixture (A) which comprises the amine salt of thiolcarbamic acid (IV), unreacted amine (I) and the special organic solvent (III) at 0° – 60°C, preferably 10° – 50°C. It is recommended that an equivalent of the alkyl halide (V) be reacted with the amine salt of thiolcarbamic acid (IV), even though the reaction velocity of the alkyl halide (V) with the unreacted amine (I) in the reaction mixture (A) is far slower than the reaction velocity of the alkyl halide (V) with the amine salt of thiolcarbamic acid (IV). If a large excess of the alkyl halide (V) is used, the unreacted amine (I) reacts with the alkyl halide (V) which produces as a byproduct, a methyleneamino compound having the formula

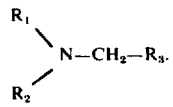

In order to insure an even and smooth reaction of the alkyl halide (V) with the reaction mixture (A), the alkyl halide (V) is preferably dissolved in the special organic solvent (III) beforehand, and then the solution is added to the reaction mixture (A).

Suitable organic solvents include those having the formula

wherein $n$ is 0,1 or 2 and R represents hydrogen, halogen or lower alkyl of 1 to 6 carbonatoms such as benzene, toluene, o-, m-, or p-xylene, ethylbenzene, chlorobenzene, dichlorobenzene, and the like.

Suitable amines (I) used in present invention include dimethylamine, diethylamine, di-n-propylamine, di-isopropylamine, di-n-butylamine, di-iso-butylamine, diamylamine, bis(2-ethylhexyl)amine, diallylamine, methylethylamine, methylbutylamine, methylphenylamine, ethylphenylamine, bis(2-hydroxyethyl)amine, dibenzylamine, pyrrolidine, piperidine, morpholine, hexylimine, and the like. Suitable alkyl halides used in present invention include the halides of alkyl or aralkyl such as, methyl, ethyl, n-propyl, iso-propyl, n-butyl, tert-butyl, α-naphthylmethyl, β-naphthylmethyl, benzyl, o-, m-, p-chlorobenzyl, o-, m-, p-bromobenzyl, o-, m-, p-iodobenzyl, o-, m-, p-fluorobenzyl, -, 2,31, 2,4-, 2,5-, 3,4-, 3,5-dichlorobenzyl, 2-, 3-, or 4-methylbenzyl, 2-, 3-, or 4-ethylbenzyl, 2-, 3-, or 4-propylbenzyl, 2-, 3-, or 4-iso-propylbenzyl, 2-, 3-, or 4-butylbenzyl, 2-, 3-, or 4-methoxybenzyl, 2-, 3-, or 4-ethoxybenzyl, 2-, 3-, or 4-propyloxybenzyl, 2-, 3-, 4-methylthiolbenzyl, 2-, 3-, or 4-ethylthiolbenzyl, 2-, 3-, or 4-nitrobenzyl, 2-, 3-, or 4-cyanobenzyl, 3-chloro or bromo-4- methoxybenzyl, 3-chloro or bromo-4-ethoxybenzyl, 3-chloro or bromo-4-methylbenzyl, 3-chloro or bromo-4-ethylbenzyl group. The halide anions include chloride, bromide and iodide.

According to present the invention, the amine salt of the thiolcarbamic acid (IV) can be stably maintained in the reaction mixture (A) if the amount of carbonylsulfide to the amine (I) is controlled within the specified limits. The unreacted amine does not react with the alkyl halide, and only the amine salt of thiolcarbamic acid reacts with the alkyl halide. Accordingly, sidereactions can be prevented to provide the product thiolcarbamate in high yield and high purity. Moreover, the contamination of the drainage solutions can be substantially reduced, thereby making the process advantageous for use on an industrial scale.

Having generally discribed this invention, a further understanding can be obtained by reference to certain specific examples which are provided herein for purpose of illustration only and are not intended to be limiting unless otherwise specified.

EXAMPLE 1

1. In a reaction vessel, 146.3 g (2.0 mole) of diethylamine was dissolved in 400 g of toluene and carbonylsulfide was introduced into the stirred solution at 15° – 20°C at a rate of 50 cm³/min. From time to time during the reaction samples of about 3 g of the reaction mixture were taken. Each sample was diluted with 100 ml of water and was titrated with 1/2N-HCl (factor: 1.025) in order to determine the inflection point of the pH curve and the concentration of the N,N-diethylamine salt of N,N-diethyl-thiolcarbamic acid in the reaction mixture. When the concentration of COS reached as high as 32.62%, which indicated that 0.958 mole of carbonylsulfide had reacted and 0.084 mole of the unreacted diethylamine remained in the reaction solution, the further introduction of COS into the reaction mixture (A) was discontinued.

2. A solution of 151.4 g (0.94 mole) of p-chlorobenzylchloride in 300 g of toluene was added dropwise to the stirred reaction mixture (A) containing 193.99 g (0.94 mole) of the N,N-diethylamine salt of N,N-diethylthiolcarbamic acid at 30° – 35°C. The solution was maintained at this temperature until the reaction was complete. The reaction mixture was washed three times with 500 ml of water, and the organic solvent layer was separated from the aqueous layer.

3. To the separated aqueous layer of step (2) was added, 45 g of sodium hydroxide and the diethylamine was recovered by distillation under reduced pressure (purity of 98.5%; yield of 98%).

4. The organic solvent layer from step (2) was washed once with 500 ml of 1N-HCl and two times with 1,000 ml of water, and then was dried over anhydrous $Na_2SO_4$. The toluene solvent was removed by distillation under reduced pressure to give the product. The amount of recovered toluene was 696.5 g (purity of 99%; yield of 99.5%).

5. According to gas chromatographic analysis of the product obtained from step (4), the product carbamate comprised 98.56% of the desired S-(p - chlorobenzyl)-N,N-diethyl-thiolcarbamate product, 0.17% of di(p-chlorobenzyl) sulfide of the formula:

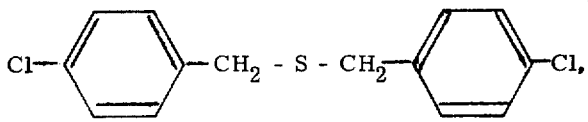

0.27% of di(p-chlorobenzyl)di-sulfide of the formula:

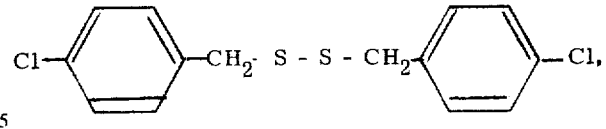

0.26% toluene, 0.07% p-chlorobenzylchloride, 0.51% p-chlorobenzalchloride and 0.15% of p-chlorotoluene as impurities.

6. After the recovery of toluene in step (4), the product was purified by distillation whereby 245.5 g (yield 99.5%) of S-(p-chlorobenzyl)-N,N-diethyl-thiolcarbamate as a colorless liquid was obtained.

7. The water used for washing in steps (3) and (4) was combined, oxidized and treated to adjust the pH by a conventional process to meet the limits of Biochemical oxygen demand (BOD) for waste water as set forth by Japanese Industrial Standard K 0102. The BOD of the waste water of the present example thus treated was only 0.007 g per gram of S-(p-chlorobenzyl) -N,N-diethyl-thiolcarbamate. On the other hand, in the conventional process for preparing S-(p-chlorobenzyl)-N,N-diethylcarbamate by reacting sodium N,N-diethyl-thiolcarbamate with p-chlorobenzylchloride, the BOD of the water used for washing was 0.136 g per gram of S-(p-chlorobenzyl)-N,N-diethyl-thiolcarbamate produced. Thus, the BOD of the wash solutions of the present example was 19 times better than the BOD of the waste water solution of the conventional process.

EXAMPLE 2

1. In accordance with the process of Example 1-(1), 146.28 g (2.0 mole) of diethylamine was dissolved in 400 g of toluene and carbonylsulfide was introduced into the solution. When the concentration of the N,N-diethylamine salt of N,N-diethyl thiolcarbamic acid reached 32.51%, which indicated that 0.955 mole of carbonylsulfide had reacted and 0.090 mole of unreacted diethylamine remained in the reaction mixture, the reaction was discontinued and the reaction mixture was kept at room temperature. Each 100 g quantity of the reaction mixture which contained 32.51 g, (0.15 mole) of the N,N-diethylamine salt of N,N-diethyl thiolcarbamic acid, was sampled at certain time intervals. In the same manner as process step 1-(2), 24.2 g (0.15 mole) of p-chlorobenzylchloride was added dropwise to the sampled reaction mixture and the resulting reaction mixture was washed with 3 portions of 50 ml of water. Also, in the same manner as process steps 1-(4), the toluene was distilled from the organic solvent layer and in accordance with process step 1-(5), the reaction product was analyzed by gas chromatography to measure the change in the N,N-diethylamine salt of N,N-diethyl thiolcarbamic acid upon aging. The results of the aging test are shown in Table 1.

TABLE 1

| Aging period of the amine salt (hr) | Purity of the product thiolcarbamate | By-product —S— | —S—S— | Unreacted starting material PCBC | T | Impurities in starting material PCDC | PCT |
|---|---|---|---|---|---|---|---|
| 0 | 98.61 | 0.19 | 0.21 | 0.05 | 0.28 | 0.50 | 0.15 |
| 24 | 98.62 | 0.19 | 0.22 | 0.05 | 0.27 | 0.51 | 0.14 |
| 48 | 98.60 | 0.19 | 0.24 | 0.06 | 0.27 | 0.50 | 0.14 |
| 72 | 98.58 | 0.21 | 0.25 | 0.04 | 0.27 | 0.50 | 0.14 |

Notes:

Thiolcarbamate 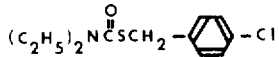

—S— 

—S—S— 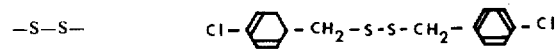

PCBC 

T 

PCDC 

PCT 

As shown in Table 1, the amine salt of thiolcarbamic acid prepared by reacting less than 0.48 mole of carbonylsulfide with 1.0 mole of the amine was stable after 72 hours aging at room temperature because of the presence of the unreacted amine, and, accordingly, the reaction mixture could be reacted with the alkyl halide to obtain the thiolcarbamate having high purity. On the other hand, however, the amine salt of thiolcarbamic acid in the reaction mixture prepared by reacting more than 0.48 mole of carbonylsulfide with 1.0 mole of the amine was unstable and could not be kept without decomposing. When the alkyl halide was added to the decomposed reaction mixture, the yield of by-products such as monosulfides and the like increased and the purity of the thiolcarbamate decreased. The results obtained from this experiment are described below as reference 1.

When a large excess of carbonylsulfide was added to 1.0 mole of the amine, the amine salt of thiolcarbamic acid was very unstable and easily decomposed because very little if any of the amine salt was present. When the alkyl halide was reacted further with the reaction mixture, large amounts of the monosulfide, disulfide, and the like by-products were formed and the purity and yield of the thiolcarbamate was substantially decreased. The results are shown in Reference 2.

REFERENCE 1

The process of EXAMPLE 2 was repeated except that 0.999 mole of carbonylsulfide was reacted with 2.0 mole of diethylamine, and thus 0.002 mole of diethylamine remained in solution. The results of the aging test are shown in Table 2.

TABLE 2

| Aging period of the amine salt | Purity of product thiolcarbamate | By-Products —S— | —S—S— | Unreacted starting material PCBC | T | Impurities in starting material PCDC | PCT |
|---|---|---|---|---|---|---|---|
| 0 | 91.87 | 2.39 | 4.75 | 0.06 | 0.27 | 0.51 | 0.15 |
| 24 | 87.92 | 4.62 | 6.49 | 0.05 | 0.26 | 0.51 | 0.14 |
| 48 | 80.65 | 6.43 | 11.93 | 0.05 | 0.27 | 0.51 | 0.15 |
| 72 | 76.86 | 9.85 | 12.37 | 0.04 | 0.27 | 0.52 | 0.15 |

REFERENCE 2

The process of Example 2 was repeated except that a large excess of carbonylsulfide was introduced even after the concentration of the N,N-diethyl amine salt of N,N-diethyl thiolcarbamic acid in the reaction mixture had reached 34.03%. The results of the aging test are shown in Table 3.

TABLE 3

| Aging period of the amine salt | Purity of product thiolcarbamate | By-Product | | Unreacted starting material | | Impurities in starting material | |
|---|---|---|---|---|---|---|---|
| | | —S— | —S—S— | PCBC | T | PCDC | PCT |
| 0 | 57.03 | 11.21 | 30.26 | 0.61 | 0.27 | 0.48 | 0.15 |
| 24 | 42.73 | 15.99 | 39.82 | 0.56 | 0.27 | 0.49 | 0.15 |
| 48 | 34.81 | 23.01 | 40.78 | 0.54 | 0.26 | 0.46 | 0.14 |
| 72 | 30.67 | 24.94 | 42.98 | 0.53 | 0.27 | 0.46 | 0.15 |

EXAMPLE 3

1. In accordance with the process described in Example 1, 90.17 g (2.0 mole) of dimethylamine was dissolved in 400 g of toluene, and carbonylsulfide was introduced into the stirred solution at 15° – 20°C at a rate of 50 cm³/min. When the concentration of the N,N-dimethylamine salt of N,N-dimethylthiolcarbamic acid in the reaction mixture has reached 26.12%, which indicated that 0.957 mole of carbonylsulfide had reacted, and that 0.086 mole of the unreacted dimethylamine remained, the reaction was discontinued whereby 538.6 g of a reaction mixture was obtained.

2. A solution of 77.3 g (0.50 mole) of 2,5-dimethylbenzylchloride in 300 g of toluene was added dropwise to 290.6 g of the stirred reaction mixture of step (1), which contained 75.90 g (0.505 mole) of the N,N-dimethylamine salt of N,N-dimethylthiolcarbamic acid at 30° – 35°C, and the mixture was kept for 3 hours at the same temperature to complete the reaction. The reaction mixture was washed with 3 portions of 500 ml of water, 500 ml of 1N-HCl and 2 portions of 1,000 ml of water. The reaction mixture was dried over anhydrous Na₂SO₄ and toluene was distilled under reduced pressure. According to the gas chromatographic analysis of the reaction product, the purity of the product as S-(2,5-dimethylbenzyl)-N,N-dimethylthiolcarbamate was 97.31%.

3. The reaction product was further purified by the distillation to give 109.6 g of S-(2,5-dimethylbenzyl)-N,N-dimethyl thiolcarbamate as a colorless liquid having a boiling point of 136° – 140°C/0.012 mmHg. (yield 98.2%).

EXAMPLE 4

1. According to the procedure of Example 1, 198.4 g (2.0 mole) of hexylimine was dissolved in 400 g of toluene and carbonylsulfide was introduced into the stirred solution at 15° – 20°C at a rate of 50 cm³ /min. When the concentration of the hexylimine salt of N,N-hexylmethylenethiolcarbamic acid reached 36.97%, which indicated that 0.942 mole of carbonylsulfide had reacted and that 0.116 mole of hexylimine remained in the reaction mixture, the reaction was discontinued whereby 645.5 g of the reaction mixture was obtained.

2. A solution of 77.9 g (0.50 mole) of ethyl iodide in 300 g of toluene was added dropwise to 350.2 g of the stirred reaction mixture of step (1), which contained 129.47 g (0.50 mole) of the hexylimine salt of N,N-hexamethylene thiolcarbamic acid, at 30° – 35°C. The mixture was kept in this temperature range for 3 hours to complete the reaction. The reaction mixture was washed 3 times with 500 ml of water, 500 ml of 1N-HCl and then 2 portions of 1,000 ml of water. The organic layer was dried over anhydrous Na₂SO₄, and toluene was distilled under reduced pressure. Gas chromatographic analysis of the product showed that the purity of S-ethyl-N,N-hexamethylene thiolcarbamate was 97.73%.

3. The product was further purified by distillation to give 91.5 g of a colorless liquid of S-ethyl-N,N-hexamethylene thiolcarbamate having a boiling point of 83°C/0.2 mmHg (yield 97.8%).

EXAMPLE 5

1. In accordance with the procedure of Example 1, 90.20 g (2.0 mole) of dimethylamine was dissolved in 400 g of toluene, and carbonylsulfide was introduced into the stirred mixture at 15° – 20°C at a rate of 50 cm³/min. When the concentration of the N,N-dimethyl amine salt of N,N-dimethyl thiolcarbamic acid reached 26.07%, which indicated that 0.954 mole of the carbonylsulfide had reacted and that 0.089 mole of the unreacted dimethylamine remained, the reaction was discontinued to give 538.1 g of the reaction mixture.

2. A solution of 110.5 g (0.5 mole) of β-naphthylmethylbromide in 300 g of toluene was added dropwise to 290.3 g of the stirred reaction mixture which contained 75.68 g (0.50 mole) of the N,N-dimethylamine salt of N,N-dimethylthiolcarbamic acid at 30° – 35°C. The mixture was kept for 3 hours at this temperature. The reaction mixture was washed 3 times with 500 ml portions of water, one-500 ml portion of 1N-HCl and then 2 portions of 1,000 ml of water. The organic layer was dried over anhydrous Na₂SO₄, and toluene was distilled under vacumm. Gas chromatographic analysis of the reaction product showed that the purity of the S-(β-naphthylmethyl)-N,N-dimethyl thiolcarbamate was 96.9%.

3. The reaction product was further purified by distillation under vacuum to give 119.9 g of a yellow viscous liquid of S-(β-naphthylmethyl)N,N-dimethyl thiolcarbamate having a boiling point of 148° – 153°C/0.02 mmHg (yield 97.8%).

EXAMPLES 6 – 20

According to the procedure of Example 1, various thiolcarbamates were prepared from various amines and various alkyl halides and carbonylsulfide in various organic solvents. In these reactions thee concentration of the amine salt of the thiolcarbamate was periodically checked to determine when to discontinue the reactions, while keeping the amount of carbonylsulfide added under a certain ratio which was less than 0.48 mole of carbonylsulfide per 1 mole of the amine. The amine salt of thiolcarbamic acid was found to be stable in every case.

Judging from the gas chromatographic analysis of the reaction product obtained by reacting the alkyl halide with the above prepared reaction mixture containing the amine salt of thiolcarbamic acid, the products contained less than 0.2% of the monosulfide, $R_3CH_2SCH_2R_3$ and less than 0.3% of disulfide, $R_3CH_2SSCH_2R_3$.

The starting materials and the results of Examples 6 - 20 are shown in Table 4, wherein the reaction temperature (1) is that of step (1) in which the amine and carbonylsulfide are reacted in the solvent; and the reaction temperature (2) is that of step (2) in which the amine salt and the alkyl halide are reacted in the solvent. The column heading "COS mole" indicates the mole ratio of carbonylsulfide per mole of amine. The purity of the product thiolcarbamates was measured from gas chromatographic analysis while the yield is based on the alkyl halide.

Table 4

| Exp.* | Amine | Solvent | React. temp. °C (1) | COS mole | Alkyl halide | temp. °C (2) | React. (boiling point) | Product |
|---|---|---|---|---|---|---|---|---|
| 6* | $(CH_3)_2NH$ | dichlorobenzene | 10–15 | 0.476 | ClCH$_2$–C$_6$H$_3$Cl$_2$ | | 30–35 | $(CH_3)_2NC(O)SCH_2$–C$_6$H$_3$Cl$_2$ |
| 7* | $(C_2H_5)_2NH$ | benzene | 15–20 | 0.476 | ClCH$_2$–C$_6$H$_4$–SCH$_3$ | | 30–35 | bp 148–150°C/0.06 mmHg; $(C_2H_5)_2NC(O)SCH_2$–C$_6$H$_4$–SCH$_3$ |
| 8* | $(C_2H_5)_2NH$ | benzene | 15–20 | 0.478 | I–C$_3$H$_5$ | | 20–25 | bp 145–158°C/0.01 mmHg; $(C_2H_5)_2NC(O)SCH_2$–CH$_3$ |
| 9* | $(CH_2=CHCH_2)_2NH$ | benzene | 15–20 | 0.475 | ClCH$_2$–C$_6$H$_4$–C$_2$H$_5$ | | 35–40 | bp 51–53°C/0.5 mmHg; $(CH_2=CHCH_2)_2NC(O)SCH_2$–C$_6$H$_4$–C$_2$H$_5$ |
| 10* | $(HOC_2H_5)_2NH$ | toluene | 15–20 | 0.477 | ClCH$_2$–C$_6$H$_4$–NO$_2$ | | 30–35 | bp 144–145°C/0.02 mmHg; $(HOC_2H_5)_2NC(O)SCH_2$–C$_6$H$_4$–NO$_2$ |
| 11* | $(C_6H_5CH_2)_2NH$ | toluene | 15–20 | 0.477 | ClCH$_2$–C$_6$H$_4$–C$_2$H$_5$ | | 35–40 | bp 150°C/0.08 mmHg; $(C_6H_5CH_2)_2NC(O)SCH_2$–C$_6$H$_4$–C$_2$H$_5$ |
| 12* | CH$_3$(n-C$_4$H$_9$)NH | benzene | 15–20 | 0.475 | ClCH$_2$–C$_6$H$_4$–OCH$_3$ | | 30–35 | bp 200–205°C/0.1 mmHg; CH$_3$(n-C$_4$H$_9$)NC(O)SCH$_2$–C$_6$H$_4$–OCH$_3$ |
| 13* | CH$_3$(n-C$_4$H$_9$)NH | benzene | 15–20 | 0.476 | ClCH$_2$–C$_6$H$_3$(OCH$_3$)Cl | | 30–35 | bp 147–150°C/0.1 mmHg; CH$_3$(n-C$_4$H$_9$)NC(O)SCH$_2$–C$_6$H$_3$(OCH$_3$)Cl |
| 14* | CH$_3$(CH$_3$O)NH | toluene | 15–20 | 0.475 | ClCH$_2$–C$_6$H$_3$Cl$_2$ | | 30–35 | bp 152–157°C/0.08 mmHg; CH$_3$(CH$_3$O)NC(O)SCH$_2$–C$_6$H$_3$Cl$_2$ |

Table 4-continued

| Exp.* | Amine | Solvent | React. temp. °C (1) | React. mole | COS | Alkyl halide | temp. °C (2) | React. (boiling point) | Product |
|---|---|---|---|---|---|---|---|---|---|

15*ʲ  C₂H₅-NH-C₆H₅    xylene   15-20   0.472   ClCH₂-C₆H₄-isoC₃H₇   30-35   bp 137/0.05 mmHg
Product: C₂H₅(C₆H₅)N-C(=O)-SCH₂-C₆H₄-isoC₃H₇

16*ᵏ  (hexamethyleneimine, H-N ring)   xylene   15-20   0.477   ClCH₂-C₆H₄-OCH₃   35-40   bp 166-168°C/0.04 mmHg
Product: ring-N-C(=O)-SCH₂-C₆H₄-OCH₃

17*ˡ  (piperidine)   toluene   15-20   0.476   ClCH₂-C₆H₄-C₂H₅   35-40   bp 170-173°C/0.2 mmHg
Product: piperidinyl-C(=O)-SCH₂-C₆H₄-C₂H₅

18*ᵐ  (piperidine)   toluene   15-20   0.473   ClCH₂-C₆H₄-Cl   35-40   mp 75°C
Product: piperidinyl-C(=O)-SCH₂-C₆H₄-Cl 19*ⁿ  (morpholine)   toluene   15-20   0.475   ClCH₂-C₆H₄-CN   35-40   mp 59-60°C
Product: morpholinyl-C(=O)-SCH₂-C₆H₄-CN 20*ᵒ  ((CH₃)₂CH-)₂NH   toluene   15-20   0.475   Cl-CH₂-C₆H₄(o-Cl)   35-40   mp 45-47°C
Product: ((CH₃)₂CH)₂N-C(=O)-S-CH₂-C₆H₄(o-Cl)
142~146°C/0.04~0.05 mmHg

*Yield (purity)
*ᵃ 96.1% (98.8%)
*ᵇ 97.6% (98.4%)
*ᶜ 98.0% (98.8%)
*ᵈ 98.4% (98.4%)
*ᵉ 96.9% (98.4%)
*ᶠ 96.4% (98.7%)
*ᵍ 98.7% (98.3%)
*ʰ 98.3% (98.1%)
*ⁱ 99.0% (98.5%)
*ʲ 98.3% (98.5%)
*ᵏ 98.8% (98.6%)
*ˡ 99.1% (98.8%)
*ᵐ 99.4% (98.5%)
*ⁿ 98.2% (98.1%)
*ᵒ 98.5% (98.8%)

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. In a process for preparing a thiolcarbamate by reacting a secondary amine having the formula $$\begin{array}{c} R_1 \\ \phantom{R}\diagdown \\ \phantom{RR}NH \\ \phantom{R}\diagup \\ R_2 \end{array}$$

wherein $R_1$ and $R_2$ are the same or different and each represent hydrogen, lower alkyl, alkoxy, alkenyl, alkoxyalkyl, cycloalkyl, hydroxyalkyl, benzyl or phenyl, or $R_1$ $R_2$ combined is a nitrogen containing heterocyclic ring with carbonylsulfide to form an intermediate of an amine salt of a thiolcarbamic acid having the formula:

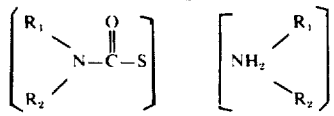

wherein $R_1$ and $R_2$ are defined as above, and then reacting the intermediate with an alkyl halide having the formula

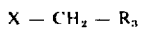

wherein X represents halogen, and $R_3$ represents hydrogen, lower alkyl, or naphthyl or phenyl which can be substituted with halogen, alkyl, alkoxy, alkylthio, cyano or nitro to yield a thiolcarbamate having the formula

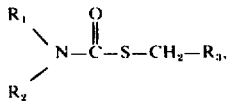

the improvement which comprises reacting said amine in a solution of an organic solvent having the formula

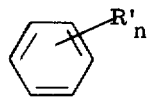

wherein n is 0, 1 or 2 and R' represents hydrogen, halogen or lower alkyl, which solvent is sparingly soluble or insoluble in water and which dissolves the amine salt of the thiolcarbamic acid, wherein less than 0.48 mole of carbonyl-sulfide per mole of the amine is added to the reaction.

2. The process of claim 1, wherein 0.48 mole – 0.10 mole of carbonylsulfide is reacted per mole of the amine, and the unreacted amine is recovered after reacting the intermediate in the presence of the amine with the alkyl halide.

3. The process of claim 1, wherein the reaction of the intermediate in the presence of the amine with the alkyl halide is performed at 0° – 60°C.

4. The process of claim 1, wherein the organic solvent is dichlorobenzene, benzene, toluene or xylene, and the amine is dimethylamine, diethylamine, di-n-propylamine, di-iso-propylamine, di-n-butylamine, di-iso-butylamine, diamylamine, bis(2-ethylhexyl)amine, diallylamine, methylethylamine, methylbutylamine, methylphenylamine, ethylphenylamine, bis(2-hydroxyethyl)amine, dibenzylamine, pyrrolidine, piperidine, morpholine or hexylimine.

5. The process of claim 1, wherein carbonylsulfide is introduced into a solution of diethyl amine in the organic solvent in a molar ratio based on the diethylamine of less than 0.48 and then p-chlorobenzyl halide is added to the reaction mixture containing free diethylamine at 0° – 60°C resulting in the formation of S-(p-chlorobenzyl)-N,N-diethyl thiolcarbamate.

6. The process of claim 1, wherein carbonylsulfide in introduced into a solution of dimethylamine in the organic solvent in a molar ratio based on the dimethylamine of less than 0.48, and then 2,5-dimethyl benzyl halide is added to the reaction mixture containing free dimethylamine at 0° – 60°C resulting in the formation of S-(2,5-dimethyl benzyl)N,N-dimethyl thiolcarbamate.

7. The process of claim 1, wherein carbonylsulfide is introduced into a solution of hexylimine in the organic solvent in a molar ratio based on the hexylimine of less than 0.48, and then ethyl halide is added to the reaction mixture containing free hexylimine at 0°– 60°C resulting in the formation of S-ethyl-N,N-hexamethylene thiolcarbamate.

8. The process of claim 1, wherein carbonylsulfide is introduced into a solution of dimethylamine in the organic solvent in a molar ratio based on the dimethylamine of less than 0.48, and then β-naphthylmethyl halide is added to the reaction mixture containing free dimethylamine at 0° – 60°C resulting in the formation of S-(β-naphthylmethyl)-N,N-dimethyl thiolcarbamate.

* * * * *